(12) United States Patent
Tsukahara et al.

(10) Patent No.: US 6,709,383 B2
(45) Date of Patent: Mar. 23, 2004

(54) DEVICE FOR DRIVING BLOOD PUMPS

(75) Inventors: Kinji Tsukahara, Seki (JP); Akira Suzuki, Nishio (JP); Hideki Wakui, Anjo (JP)

(73) Assignee: Aisin Seiki Kabushiki Kaisha, Kariya (JP)

( * ) Notice: Subject to any disclaimer, the term of this patent is extended or adjusted under 35 U.S.C. 154(b) by 324 days.

(21) Appl. No.: 09/986,877

(22) Filed: Nov. 13, 2001

(65) Prior Publication Data

US 2003/0069466 A1 Apr. 10, 2003

(30) Foreign Application Priority Data

Nov. 10, 2000 (JP) ........................................ 2000-344451

(51) Int. Cl.[7] ................................................ A61M 1/10
(52) U.S. Cl. .......................................... 600/16; 623/3.21
(58) Field of Search ...................... 600/16–18; 623/3.16, 623/3.1, 3.21

(56) References Cited

U.S. PATENT DOCUMENTS

| | | | | |
|---|---|---|---|---|
| 3,604,016 A | * | 9/1971 | Robinson et al. | 623/3.21 |
| 3,680,981 A | * | 8/1972 | Wagner | 417/388 |
| 4,243,530 A | * | 1/1981 | Lehnhoff et al. | 210/137 |
| 4,648,385 A | | 3/1987 | Oumi et al. | |
| 5,269,811 A | * | 12/1993 | Hayes et al. | 623/3.24 |
| 5,353,646 A | * | 10/1994 | Kolpak | 73/861.04 |
| 6,443,884 B1 | * | 9/2002 | Miyawaki | 600/17 |

OTHER PUBLICATIONS

"Diagnosis of Mechanical Failures of Total Artificial Hearts", Y. Taenaka et al (vol. XXXI Trans Am Soc Artif Intern Organs 1985, pp. 79–81.

* cited by examiner

*Primary Examiner*—Kennedy Schaetzle
(74) *Attorney, Agent, or Firm*—Oblon, Spivak, McClelland, Maier & Neustadt, P.C.

(57) ABSTRACT

A blood pump driving device which is capable of making a blood pump 10 free from an unbalance between loads when sucking and discharging, respectively and which makes it possible to eliminate a sensor positioned close to a patient, is made up of an oil reservoir 30 including therein a gas chamber 33 and a liquid chamber 32, an oil pump 20 for pumping out a liquid stored in the liquid chamber 32 of the oil reservoir 30 to the blood pump 10, and a pressure accumulating chamber 34 storing therein a gas pressure of the gas chamber 33 of the oil reservoir 30 by being brought into fluid communication with the gas chamber 33 of the oil reservoir 30.

10 Claims, 5 Drawing Sheets

DEVICE FOR DRIVING BLOOD PUMPS

The present application is based on, and claims priority under 35 U.S.C § 119 from, Japanese Patent Application No. 2000-344451 filed on Nov. 10, 2000, the entire contents of which is incorporated herein by reference.

BACKGROUND OF THE INVENTION

1. Field of the Invention

The present invention is generally directed to a device for driving a blood pump, which is used for blood circulation in a living body or for assisting blood circulation in a living body, such as an artificial heart pump or an in-aortic balloon pump. More particularly, the present invention is directed to a device which detects a volume of blood pumped from a blood pump, the device including an oil reservoir in which are provided a gas chamber, a liquid chamber, and a movable member separating the two chambers, pump means for pumping out an amount of blood stored in the liquid chamber of the oil reservoir to the blood pump, and a pressure accumulating chamber storing therein a gas pressure of the gas chamber of the oil reservoir by being brought into fluid communication with the gas chamber of the oil reservoir.

2. Background Art

In a blood pump which is in association with a living body, the pumping capacity is necessary for confirming whether or not the blood pump is properly operating and for detecting a current state of the living body.

In addition, in order to obtain the maximum volume of blood pumped from the blood pump, it is desired to fully utilize the pump by monitoring its stroke. That is to say, the desired control of the pump is to pump blood out when the blood pump is filled with blood, and immediately thereafter to pump blood into the blood pump.

Conventionally, a device has been provided which operates based on a blood flow amount measured by a flow instrument placed in a conduit between the blood pump and the living body. In addition, a method has been provided which measures a displacement of a piston of a blood pump by providing a position detection sensor, as U.S. Pat. No. 4,648,384. Moreover, in the publication entitled "Diagnosis of Mechanical Failures of Total Artificial Hearts" (Vol. XXXI, Trans. Am. Soc. Artif. Intern. Organs 1985, pp.79–81), an integrated value of an air flow amount is calculated when released to atmospheric pressure, in order to determine an air amount which is used to drive a blood pump.

However, in the first and second-mentioned methods, a precise measuring instrument has to be placed close to the patient, which requires long wiring between the instrument and a monitor which is spaced from the patient, resulting in a problem that the patient is limited in his/her actions or behavior in view of patient safety.

As for the third-mentioned method, the requirement of integrating the airflow amount causes problems such as measuring precision and measuring device equipment complexity.

Moreover, due to the fact that the blood load becomes larger when blood is pumped-out, if the blood pump is designed to be driven by a single bi-directional motor, its control becomes complex, which consumes much electric power, with the result that making a device for controlling such a motor smaller is difficult.

Due to the fact that the blood load becomes larger when blood is pumped-out, the rotation speed of the motor becomes much larger when blood is pumped-out than when blood is pumped-in, which causes the rotation speed of the motor to peak when blood is pumped-out, resulting in a problem that the pumped-out amount of blood fails to increase.

Thus, a need exists to provide a device for driving a blood pump which overcomes the aforementioned problems.

SUMMARY OF THE INVENTION

The present invention has been developed to satisfy the need noted above. A first aspect of the present invention provides a device for driving a blood pump which comprises an oil reservoir including therein a gas chamber and a liquid chamber which are separated by a movable member; pump means for pumping out a liquid stored in the liquid chamber of the oil reservoir to the blood pump; and a pressure accumulating chamber storing therein a gas pressure of the gas chamber of the oil reservoir by being brought into fluid communication with the gas chamber of the oil reservoir.

A second aspect of the present invention is to provide a device which further comprises pressure measuring means for determining the gas pressure in the gas chamber of the oil reservoir.

A third aspect of the present invention is to provide a device, wherein the pressure measuring means is provided in the pressure accumulating chamber in order to determine the gas pressure in the gas chamber of the oil reservoir.

A fourth aspect of the present invention is to provide a device for driving a blood pump which comprises a first port connected to the blood pump; a second port connected to a liquid chamber of an oil reservoir which is separated therein from a gas chamber by a movable member; pump means for establishing positive and negative pumping actions in alternate fashion, the positive pumping action and the negative pumping action sucking and discharging a liquid from the second port and the first port to discharge the liquid to the first port and the second poll, respectively; pressure measuring means for determining a pressure in the gas chamber of the oil reservoir; and a control device controlling the positive and negative pumping actions of the pump means on the basis of a signal issued from the pressure measuring means.

A fifth aspect of the present invention is to provide a device, wherein the control device calculates an amount of the liquid to be sucked from and discharged to the blood pump on the basis of a changed amount in the signal from the pressure measuring means.

A sixth aspect of the present invention is to provide a device, wherein the control device switches, on the basis of the signal from the pressure measuring means, the pumping means from a positive pumping action to a negative pumping action and vice versa.

A seventh aspect of the present invention is to provide a device, wherein the gas chamber is in association with the atmosphere by way of valve means so as to be brought into atmospheric pressure level when the pressure in the gas chamber becomes a negative pressure.

An eighth aspect of the present invention is to provide a device, wherein one of a capacity of the gas chamber and the pressure in the gas chamber is set in order that loads of the pumping means when doing the respective positive and negative pumping actions are made as equal as possible.

A ninth aspect of the present invention is to provide a separation chamber including a second liquid chamber and a second gas chamber which is separated by a second movable member, the second liquid chamber being connected to the first port, the second chamber being connected to the blood pump.

A tenth aspect of the present invention is to provide a device, wherein the control device sets an amount of air in the second gas chamber on the basis of the signal from the pressure measuring means.

In accordance with the first aspect of the present invention, the blood pump driving device is provided with a pressure accumulating chamber storing therein a gas pressure of the gas chamber of the oil reservoir by being brought into fluid communication with the gas chamber of the oil reservoir. This pressure accumulating chamber acts as a load of the pump means during its pump-in process wherein the liquid filled in the liquid chamber of the oil reservoir is discharged to the blood pump, while the resulting pressure or stored pressure in the pressure accumulating chamber assists the pump means during its pump-out process. This eliminates load unbalance in the pump means.

In accordance with the second aspect of the present invention, in addition to the structure of the first aspect, the blood pump driving device further includes the pressure measuring means for determining the gas pressure in the gas chamber of the oil reservoir, which makes it possible to establish a control based on the gas pressure in the gas chamber and to eliminate a sensor to be placed close to the patient.

In accordance with the third aspect of the present invention, in the blood pump driving device which is a modified structure of the second aspect, the pressure measuring means is provided in the pressure accumulating chamber in order to determine the gas pressure in the gas chamber of the oil reservoir. This makes it possible to establish a control based on the determined gas pressure in the gas chamber of the oil reservoir.

In accordance with the fourth aspect of the present invention, in the blood pump driving device, the control device controls the positive and negative pumping actions of the pump means on the basis of the signal issued from the pressure measuring means, the positive pumping action being made to discharge the liquid to the first port which is sucked from the second port, the negative pumping action being made to discharge the liquid to the second port which is sucked from the first port. This equalizes the loads of the pump means during its respective opposite direction rotations and makes it unnecessary to place a sensor near the patient.

In accordance with the fifth aspect of the present invention, in the blood pump driving control device which is of a modified structure of the fourth aspect, the control device calculates the amount of the liquid to be sucked from and discharged to the blood pump on the basis of the changed amount in the signal from the pressure measuring means. This makes it possible to establish a control based on the determined amount of liquid discharged to or sucked from the blood pump, thereby making a control of the amount of blood which is discharged to or sucked from the living body more precise.

In accordance with the sixth aspect of the present invention, in the blood pump driving device which is of a modified the structure of the fourth aspect, the control device switches, on the basis of the signal from the pressure measuring means, the pumping means from the positive pumping action to the negative pumping action and vice versa. This equalizes the loads of the pump means during its respective normal and reverse rotations.

In accordance with the seventh aspect of the present invention, in the blood pump driving device which is of a modified structure of the fourth aspect, the gas chamber is in association with the atmosphere by way of valve means so as to be brought to atmospheric pressure when the pressure in the gas chamber becomes negative pressure. This causes the pressure in the gas chamber not to be always negative, thereby properly maintaining the amount of gas in the gas chamber.

In accordance with the eighth aspect of the present invention, in the blood pump driving device which is of a modified structure of the fourth aspect, one of a capacity of the gas chamber and the pressure in the gas chamber is set in order that loads of the pumping means when doing the respective positive and negative pumping actions are made as equal as possible. This equalizes the loads of the pump means during its respective normal and reverse rotations.

In accordance with the ninth aspect of the present invention, in the blood pump driving device which is structured to add the separation chamber to the fourth aspect such that the separation chamber includes the second liquid chamber and the second gas chamber which is separated by a second movable member, the second liquid chamber being connected to the first port, the second chamber being connected to the blood pump. This makes it possible for the blood pump to be air-pressure operated.

In accordance with the tenth aspect of the present invention, in the blood pump driving device which is of a modified structure of the ninth aspect, the control device sets the amount of air in the second gas chamber on the basis of the signal from the pressure measuring means. This makes it possible to establish a control based on the set amount of air in the second gas chamber.

BRIEF DESCRIPTION OF THE DRAWINGS

The above and other objects, features and advantages of the present invention will be more apparent and more readily appreciated from the following detailed description of preferred exemplary embodiments of the present invention, taken in connection with the accompanying drawings, in which.

DETAILED DESCRIPTION OF THE PREFERRED EMBODIMENTS

Hereinafter, embodiments of the present invention will be described in great detail with reference to the attached drawings.

First Embodiment

Figure 1:
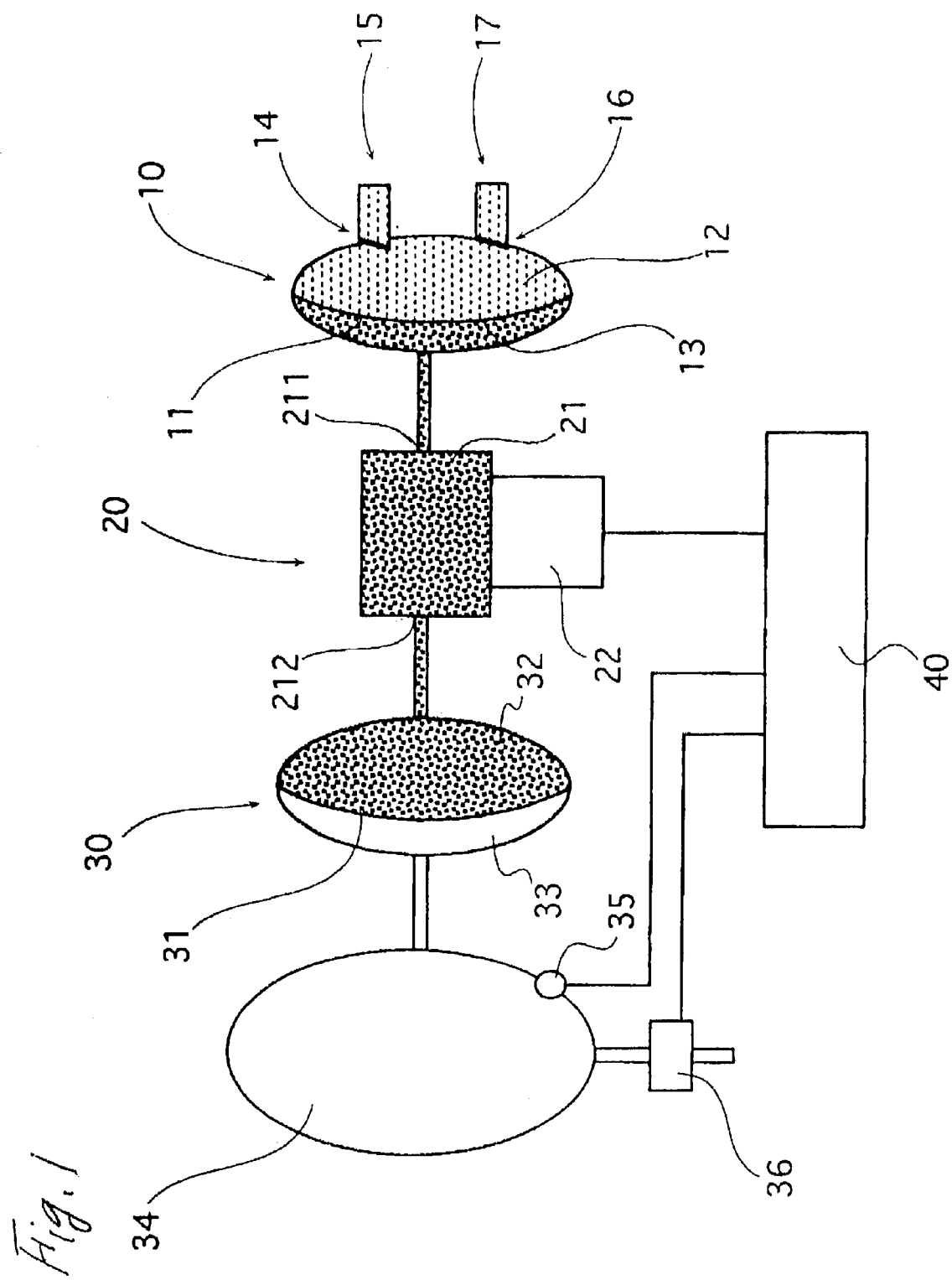
FIG. 1 illustrates a block diagram of a device for driving a blood pump in accordance with a first embodiment of the present invention.

Referring first to FIG. 1, there is illustrated a block diagram of a device for driving a blood pump in accordance with a first embodiment of the present invention. The device includes an oil reservoir 30 having therein an air chamber 33 as a gas chamber and a liquid chamber 32, an oil pump 20 as a pump means, which pumps out a liquid filled in the liquid chamber 32 of the oil reservoir 30, a blood pump 10 which pumps out/in blood by the pumped-out liquid from the oil pump 20, and a pressure accumulating chamber 34 storing therein a gas pressure of the gas chamber 33 of the oil reservoir 30 by being in fluid communication with the gas chamber 33 of the oil, reservoir 30.

In the oil reservoir 30, there is provided a diaphragm 31 as a movable member, which establishes a separation between the air chamber 33 and the liquid chamber 32. The air chamber 33 of the oil reservoir 30 is in fluid communication, by way of a conduit with the pressure accumulating chamber 34 which stores therein the gas pressure in the gas chamber 34.

The oil pump 20 is made up of a pump chamber 21 and a motor 22. The pump chamber 21 includes a housing and a rotor (neither is shown). The motor 22 is connected to rotate the rotor. The oil pump 20 is designed to perform bi-directional pump actions in alternate fashion. A positive pump action pumps a liquid to a first port 211 from a second port 212, while a negative pump action pumps the liquid to the second port 212 from the first port 211.

In the blood pump 10, a blood chamber 12 and a liquid-operated chamber 13 are separated by a diaphragm 11 as a movable member. The blood chamber 12 is filled with blood, while the liquid-operated chamber 13 is supplied with the liquid from the pump chamber 21. The liquid filled in the liquid-operated chamber 13 is an incompressible liquid such as a silicon oil.

The blood chamber 12 is provided with a blood-in port 14 with a one-way valve 14 which permits blood-in only. The port 14 is connected, by way of a conduit (not shown), to a portion such as an atrium of a living body (not shown). The blood chamber 12 is also provided with a blood-out port 17 with a one-way valve 16 which permits blood-out only. The port 17 is connected, by way of a conduit (not shown), to an aorta of the living body.

A control device 40, whose principal component is a micro-processor, is connected to a pressure sensor 35 which is provided in the pressure accumulating chamber 34, is also connected to an open/close valve 36 which is provided in a conduit terminated in the chamber 34, and is also connected to the motor 22 of the oil pump 20. The control device 40 is designed or constructed to control the open/close valve 36 and the motor 22 on the basis of an electric signal which is shaped by a pressure wave form resulting from a pulsative beat of the blood pump 10 which is detected or determined by the pressure sensor 35.

Figure 2:
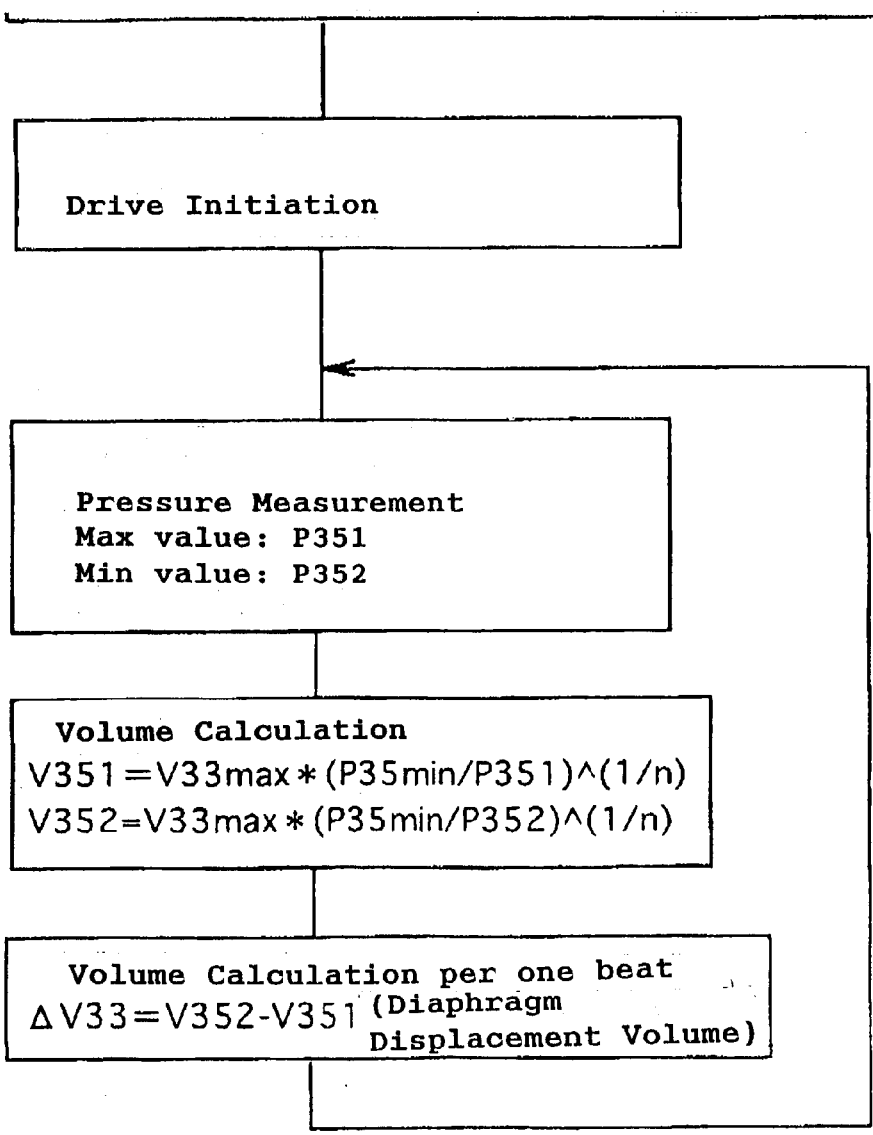
FIG. 2 illustrates a flowchart which indicates a control procedure of the device illustrated in FIG. 1.

An operation of the device having the aforementioned structure will be described herein below with reference to a flowchart depicted in FIG. 2.

The liquid-operated chamber 13 in the blood pump 10 is filled with the incompressible liquid such as silicon oil. When the silicon oil is pumped out, the diaphragm 11 is deformed or displaced to expand the blood chamber 12, which introduces therein the blood from the living body. On the other hand, when the silicon oil is introduced into the liquid-operated chamber 13, the blood is pumped out from the blood chamber 12 to the living body.

The oil pump 20 feeds the silicon oil from the liquid reservoir 30 to the blood pump 10 while the motor 22 is being driven in positive (normal) rotation, while the oil pump 20 feeds the silicon oil from the blood pump 10 to the liquid reservoir 30 while the motor 22 is being in negative (reverse) direction. Thus, the pressure in the pressure accumulating chamber 34 is made lower or raised when the silicon oil is sucked into or discharged from the blood pump 10, respectively, which produces a pressure wave depending on the repetitive beat (i.e., pulsative movement) of the blood pump 10. Such a pressure wave is taken into or fed into the control device 40. The pressure accumulating chamber 34 is selectively exposed to the atmosphere by way of the open/close valve 36.

The control device 40 closes the open/close valve 36 to isolate the pressure accumulating chamber 34 for sealing the same by doing a preparatory operation which is performed prior to the pumping operation, for bringing the volume of the blood chamber 12 in the blood pump 10 into its minimum value, which is established by driving the motor 22 in the normal direction with the open/close valve 36 opened, i.e., which is established by maintaining the diaphragm at its fully pushed stroke position.

It is to be noted that for the prevention of excess force on the diaphragm, the rotation speed of the motor 22 is adjusted to set the silicon oil pressure at about 100–200 mmHg. A bypass circuit (not shown) may be provided between the discharging and sucking sides of the pump chamber 21 in case the silicon oil pressure rises above the set value. Accordingly, the pressure of the sealed air chamber made up of the air chamber 33 and the pressure accumulating chamber 34 is P35min in minimum and is equal to the atmospheric pressure, and the volume of the sealed air chamber is V33max in maximum.

Next, when the silicon oil is discharged from the blood pump 10 to maximize the volume of the blood chamber 12 in the blood pump 10, i.e., to transfer the diaphragm 11 to its fully stroked end, the air pressure and the volume of the sealed air chamber become P35max in maximum and V33min in minimum, respectively.

When the pressure in the sealed air chamber is P35, the volume V33 of the sealed air chamber is expressed as follows by the politropic change formula:

$$V33 = V33\text{max} \times (P35\text{min}/P35)^{\wedge}(1/n).$$

P35min is the atmospheric pressure as mentioned above and V33max is given by design. Due to the fact that this capacity V33 is converted into the capacity of the liquid chamber 32 in the oil reservoir 30 and the capacity of the liquid-operated chamber 13 in the blood pump 10, the capacity of the blood chamber 12, i.e., the stroke amount of the blood pump 10, can be calculated. That is to say, the capacity of the blood chamber 12 in the blood pump 10 is expanded by (V33max−V33), i.e., V33max×(P35min/P35)^(1/n), when compared to the fully discharged or minimum capacity of the blood chamber 12, which makes it possible to calculate the stroke amount of the diaphragm. Thus, the control device 40 can indirectly determine the position of the diaphragm 11 on the basis of the pressure wave form issued from the pressure sensor 35.

When the pumping action is initiated, the pressure waveform goes up and down alternately between specific maximum and minimum respective values P351 and P352. At this time, the absolute value of the sealed air chamber capacity change Δ V33 is calculated, like the above, from the formula:

$$\Delta V33 = V33\text{max} \times ((P35\text{min}/P351)^{\wedge}(1/n) - ((P35\text{min}/P352)^{\wedge}(1/n)).$$

This capacity change Δ V33 is equal to the capacity change in the liquid chamber 32 of the oil reservoir 30 and is also equal to the change amount in the blood chamber 12 of the blood pump 10, which is the pumping amount of the blood pump 10. Thus, the pressure waveform issued from the sensor 35 provides the amount of the blood pumped out from the blood pump 12.

The control device 40 turns the motor 22 in a positive direction immediately when the pressure P fed from the pressure sensor 35 is increased, to a maximum threshold value which is almost P35max during reverse rotation of the motor 22. This maximum threshold value is set to be slightly smaller than P35max in view of a time delay such as a time duration required for direction change in rotation of the motor 22, which makes it possible to not apply an excessive force to the diaphragm 11 in the blood pump 10, thereby enhancing the reliability thereof.

The control device 40 turns the motor 22 in the negative direction immediately when the pressure P fed from the pressure sensor 35 is reduced to a minimum threshold value which is almost P35min during positive rotation of the motor 22. This minimum threshold value is slightly higher than Pmin in view of time delay, which makes it possible to not apply an excessive force to the diaphragm 11 in the blood pump 10, thereby enhancing the reliability thereof. Repeating the above-mentioned alternation controls the pumping action, wherein the blood pump 10 repeats full blood suction and full blood discharge blood. It is to be noted that the above P35max and P35min are previously set as a result of monitoring the operation of the blood pump 10.

Due to the fact that the pressure in the pressure accumulating chamber 34 increases to resist or assist the rotation of the fluid pump 20 during its reverse rotation with less load or normal rotation with much load, respectively, it is possible to equalize the load in pump normal direction rotation and the load in pump reverse direction rotation.

In the blood pump driving device which operates as mentioned above, the pressure accumulating chamber 34 is in fluid communication with the air chamber 33 for storing the pressure therein, whereby the pressure accumulating chamber 34 acts as the load of the oil pump 20 while the oil pump 20 is in its sucking process for discharging the silicon oil filled in the liquid chamber 32 of the oil reservoir 30 to the blood pump 10. On the other hand, the pressure stored in the pressure accumulating chamber 34 acts as an assist for the oil pump 20 while the oil pump 20 is in its discharging or pump-out process. Thus, load unbalance of the blood pump 10 can be eliminated.

In detail, while the blood pump 10 is in its discharging or pump-out process, the required pump head requirement of the oil pump 20 is much higher than while the blood pump is in its sucking or pump-in process. The pressure accumulating chamber 34 becomes a load of the oil pump 20 while the blood pump is in its sucking or pump-in process, and the pressure stored in the pressure accumulating chamber 34 serves for driving the oil pump 20 while the blood pump is in its sucking or pump-in process, resulting in elimination of the load unbalance between the foregoing processes.

In addition, the pressure in the pressure accumulating chamber 34 is maximized when the blood pump 10 is transferred from the last stage of the sucking process to an initial stage of the discharging process. In view of the fact that sometimes the rising-up speed of the driving pressure of the blood pump 10 at the initial stage of discharging process of the blood pump 10 is an important factor, utilizing the maximum pressure in the pressure accumulating chamber 34 can satisfy such a requirement, thereby improving the rising-up speed.

Furthermore, without the pressure accumulating chamber 34, the air chamber 33 is open, which requires a filter for preventing damage to the diaphragm 31 by the possible entry of foreign particles. In light of the fact that the filter has to be periodically maintained to prevent clogging, providing the pressure accumulating chamber 34 permits the air chamber 33 to be sealed, which eliminates the filter and periodic maintenance.

In the above blood pump driving device in accordance with the first embodiment, due to the fact that the pressure sensor 35 detects or determines the internal pressure of the air chamber 33 in the oil reservoir 30, a control can be established on the basis of the detected internal pressure, and the need for a sensor placed near the patient is eliminated.

In the above blood pump driving device in accordance with the first embodiment, due to the fact that the pressure sensor 35 is placed in the pressure accumulating chamber 34 which is located far away from the patient, a control can be established on the basis of the detected pressure in the pressure accumulating chamber 34 and the need for a sensor placed near the patient is eliminated.

In the above blood pump driving device in accordance with the first embodiment, on the basis of the signal issued from the pressure sensor 35 which is representative of the pressure in the air chamber 33, the control device 40 alternately instructs positive and negative pump actions of the oil pump 20, the positive pump action pumping out the oil which is pumped in from the second port 212 to the first port 211, the negative pump action pumping out the oil which is pumped in from the first port 211 to the second port 212. Thus, the loads of the oil pump 20 when driven in the respective positive and negative directions can be equalized and no sensor provided close to the patient is required.

Moreover, in the blood pump driving device in accordance with the first embodiment, on the basis of the change amount in the signal issued from the pressure sensor 35, the control device 40 calculates the amount of the oil sucked into (discharged from) the blood pump 10, which makes it possible to establish a control on the basis of the calculated amount of the oil sucked into (discharged from) the blood pump 10, resulting in a very precise control of the amount of blood fed from (to) the living body.

In the blood pump driving device in accordance with the first embodiment, on the basis of the signal issued from the pressure sensor 35, the control device 40 switches between the positive and negative pumping actions of the oil pump 20, which makes it possible to equalize the loads when the oil pump 20 is in positive and negative rotations, respectively.

Furthermore, in the blood pump driving device in accordance with the first embodiment, the air chamber 33 is brought into fluid communication with the atmosphere by way of the open/close valve 36 as valve means, which brings the pressure in each of the pressure accumulating chamber 34 and the air chamber 33 into atmospheric pressure level when the pressure in the air pressure in the air chamber 34 becomes negative, so that the air chamber 33 is prevented from being kept at negative pressure, thereby to maintain the amount of air at a proper level.

In the blood pump driving device in accordance with the first embodiment, the capacity and/or pressure of the air chamber 33 are set so that the loads of the oil pump 20 when in its respective positive and negative pumping actions are as equal as possible.

Second Embodiment

A blood pump driving device in accordance with a second embodiment is identical with the blood pump driving device in accordance with the first embodiment, except that the former driving device employs an air-operated blood pump instead of the liquid-operated blood pump in the former driving device. Hereinafter, only such a difference is detailed.

Figure 3:
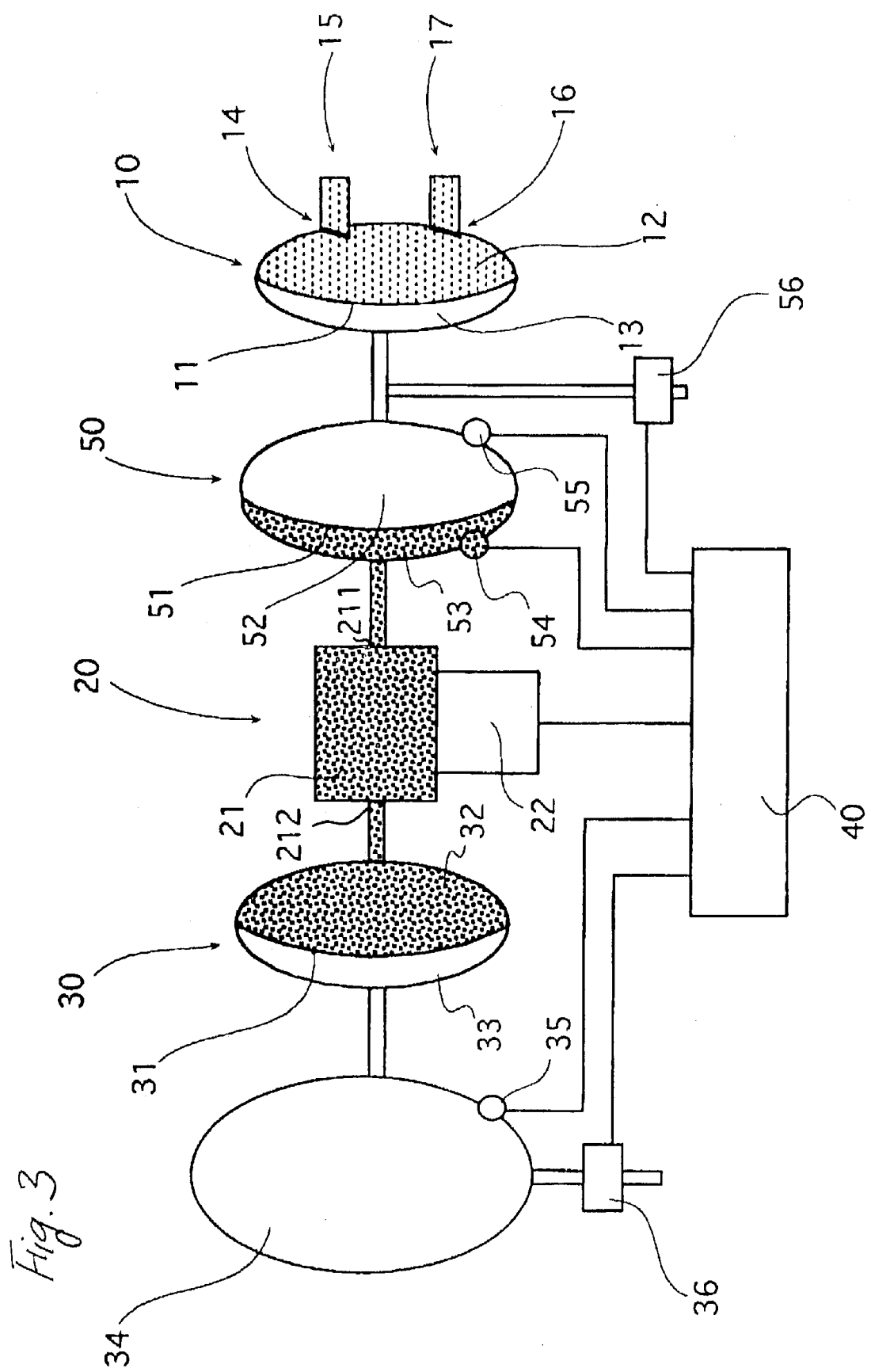
FIG. 3 illustrates a block diagram of a device for driving a blood pump in accordance with a second embodiment of the present invention.

The blood pump driving device which is illustrated in FIG. 3 has a separating chamber device 50 between the blood pump 10 and the oil pump 20 of the blood pump driving device depicted in FIG. 1. In the structure in FIG. 3, an internal space of the separating chamber device 50 is divided by a diaphragm 51 into a gas chamber 52 and a liquid chamber 53 which are in fluid communication with a gas driving chamber 13 of the blood pump 10 and a pump chamber 21 of an oil pump 20, respectively.

Pressure sensors 55 and 54 are provided in the air chamber 52 and the liquid chamber 53, respectively. The air chamber 52 is capable of opening to the atmosphere by way of an open/close valve 56. The open/close valve 56 opens to suck in the atmosphere when a pressure indication of the pressure sensor 54 is in excess of a pressure indication of the pressure sensor 55, which is indicative of an air amount insufficiency or shortage in a sealed space made up of the air chamber 52 and the air operation chamber 13. On the other hand, the open/close valve 56 opens to discharge the atmospheric pressure when the pressure indication of the pressure sensor 55 is in excess of the pressure indication of the pressure sensor 54, which is indicative of an air amount excess in the sealed space between the air chamber 52 and the air operation chamber 13. Such atmospheric pressure sucking and discharging maintain the amount of air in the sealed space at a suitable level.

Figure 4:
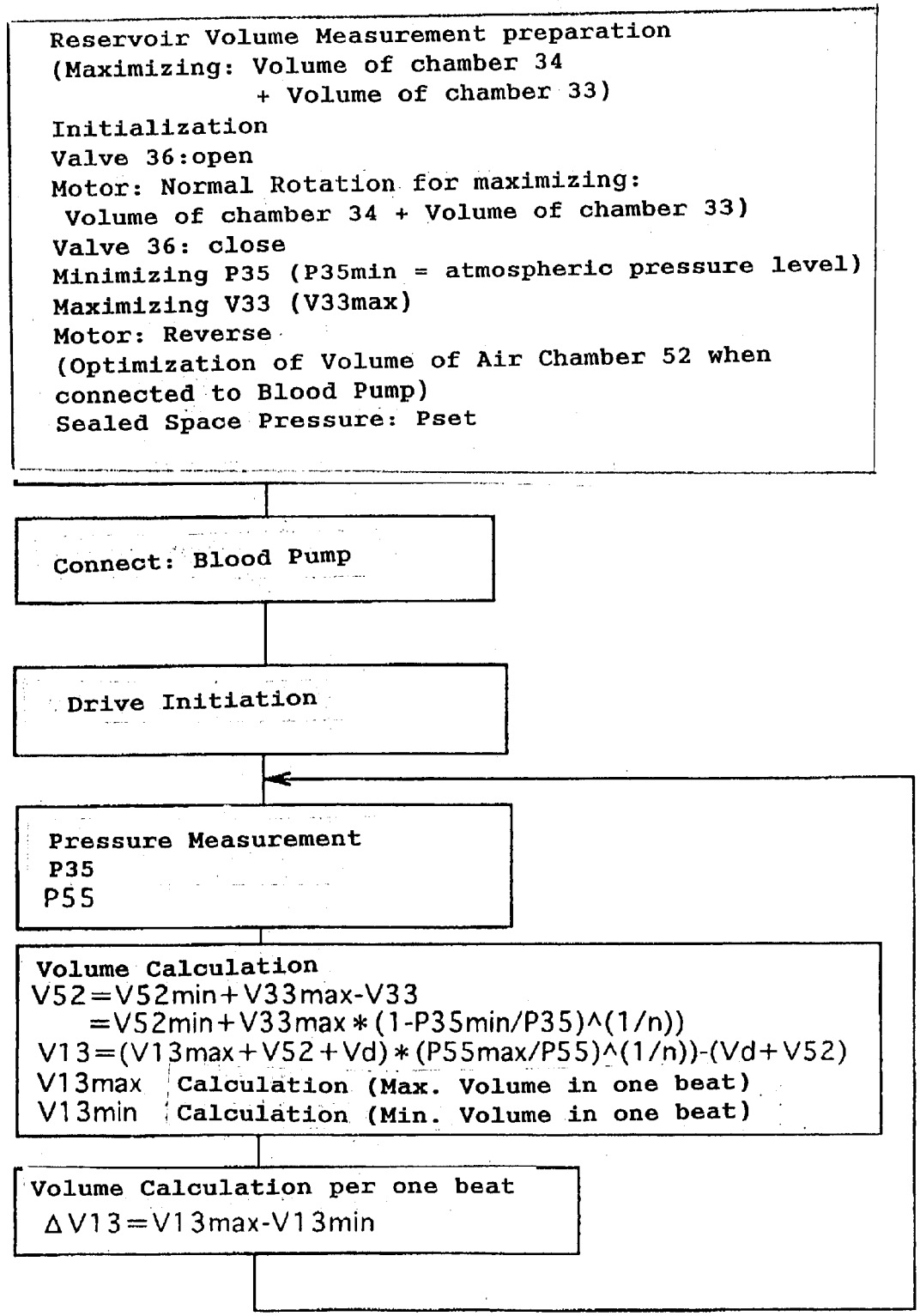
FIG. 4 illustrates a flowchart which indicates a control procedure of the device illustrated in FIG. 3.

According to a control which follows a flowchart in FIG. 4, a control device 40 always closes the open/close valve 36 and the open/close valve 56 to isolate the pressure accumulating chamber 34 and the air chamber 52 from the atmosphere. In a preparatory operation which is performed prior to a connection of the blood pump 10 to the separating chamber device 50, first of all, the open/close valve 36 is opened, a motor 22 is driven to rotate in normal direction, thereby displacing the diaphragm 51 to its fully stroked position, and while maintaining the resultant condition the open/close valve 36 is closed.

At this stage, the pressure in the sealed space between the air chamber 33 and the pressure accumulating chamber 34 becomes minimum pressure level P35min which is equal to the atmospheric pressure level, and the volume or capacity of the sealed space becomes the maximum level V33max. Next, the motor 22 is reversed, creating a condition which causes the pressure in the sealed space to be Pset, and the resulting state is maintained.

At this time, the capacity or volume of the sealed space can be found, according to the pressure indication of the pressure sensor 35, i.e., $$Vset = V33max \times (P25min/Pset)^{(1/n)}.$$

Setting the Vset to be optimum means an optimization of the volume of the air chamber 52, and under the resulting state if the blood pump 10 is connected with the separating chamber device 50 it becomes possible to initiate the blood pump 10 under a suitable condition in air amount in the sealed space made up of the air chamber 52 and the air driving chamber 13.

The control device 40 always compares the pressure waveforms issued from the respective pressure sensors 54 and 55. While the blood pump 10 is being driven, if the pressure indication of the pressure sensor 54 is in excess of the pressure indication of the pressure sensor 55 because of a variation of the air amount in the sealed space between the air chamber 52 and the air-driving chamber 13, due to insufficient air in the sealed space which results from the diaphragm 51 reaching the fully stroked position at the side of the air chamber 52, the open/close valve 56 is opened to introduce atmospheric pressure in the sealed space in synchronization with a negative pressure indication of the pressure sensor 55.

In the event that the pressure indication of the pressure sensor 55 exceeds the pressure indication of the pressure sensor 54, which means that the amount of air in the sealed space between the air chamber 52 and the air driving chamber 13 becomes excess, the open/close valve 56 is opened to discharge a surplus amount of air in synchronization with a positive pressure indication of the pressure sensor 55.

In addition, the rotation speed of the motor 22 in normal or reverse direction is increased until the diaphragm 11 reaches the corresponding fully stroked position. At this time, the pressure waveform of the pressure sensor 55 or 54 is indicative of a specific maximum level P55max or a specific minimum P55min. Next, as soon as the pressure indication of the pressure sensor 55 or 54 becomes the maximum value P55max, i.e., the diaphragm 51 is placed close to its fully stroked position at the side of the air chamber 52, the open/close valve 36 is closed.

Thus, the pressure indication of a pressure sensor 35 is set to be the maximum level P35min which is equal to the atmospheric level, and at this time the volume of the sealed space is at its maximum level V33max. When the pressure indication of the pressure sensor 55 or 54 becomes its minimum level P55min, the pressure indication of the pressure sensor 35 becomes its maximum level P35max and the volume of the sealed space at this time becomes its minimum level V33min.

When the pressure indication of the pressure sensor 55 of the sealed space becomes P35, the volume of the sealed space V33 is calculated by the formula $$V33 = V33max \times (P35min/P35)^{(1/n)}.$$

As mentioned above, P35min is the atmospheric pressure level and V33max is given by design, which makes it possible to find the absolute value of this volume V33. The volume V33 is converted into the volume of the liquid chamber 32 in the oil reservoir 30, the liquid chamber 53 in the separating chamber device 50, and the volume of the air chamber 52. In detail, the volume V52 of the air chamber 52 is increased, by a difference between V33max and V33, i.e., $V33max \times (1-(P35min/P35)^{(1/n)})$ and becomes $V52 = V52min + V33max \times (1-(P35min/P35)^{(1/n)})$.

At this time, letting the pressure of the air chamber 13 in the blood pump 10 and the volume of piping between the air chamber 53 and the air driving chamber 13 be P55 and given Vd, respectively, the volume V13 of the air chamber 13 in the blood chamber 10 can be found from the formula $$V13 = (V13max + V52min + Vd) \times (P55max/P55)^{(1/n)} - (Vd + V52).$$

Thus, the changing amount of P55 is converted into the volume of the air-driving chamber 13 in the blood pump 10, which makes it to find the volume of the blood chamber 12, i.e., the stroke change in the blood pump 10.

As mentioned above, during pumping actions, on the basis of the pressures P35 and P55 in two chambers, i.e., the pressure indications of the respective pressure sensors 35 and 55, the pumped-out blood amount can be found. It is to be noted that the control is similar to the first embodiment for the full-sucking and full-discharging controls for the blood pump 10.

The blood pump driving device in accordance with the second embodiment includes the separating chamber device 50 in which the liquid chamber 53 as a second liquid chamber is separated from the air chamber 52 as a second air chamber by the diaphragm 51, the liquid chamber 53 being in fluid communication with the first port 211, the air chamber 52 being in fluid communication with the blood pump 10, thereby the blood pump 10 can be an air pressure operated blood pump.

In addition, in the blood pump driving device in accordance with the second embodiment, the control device 40 sets the amount of air in the air chamber 53 on the basis of the pressure indication of the pressure sensor 55, which makes it to perform control on the basis of the air amount in the air chamber 53.

Third Embodiment

Figure 5:
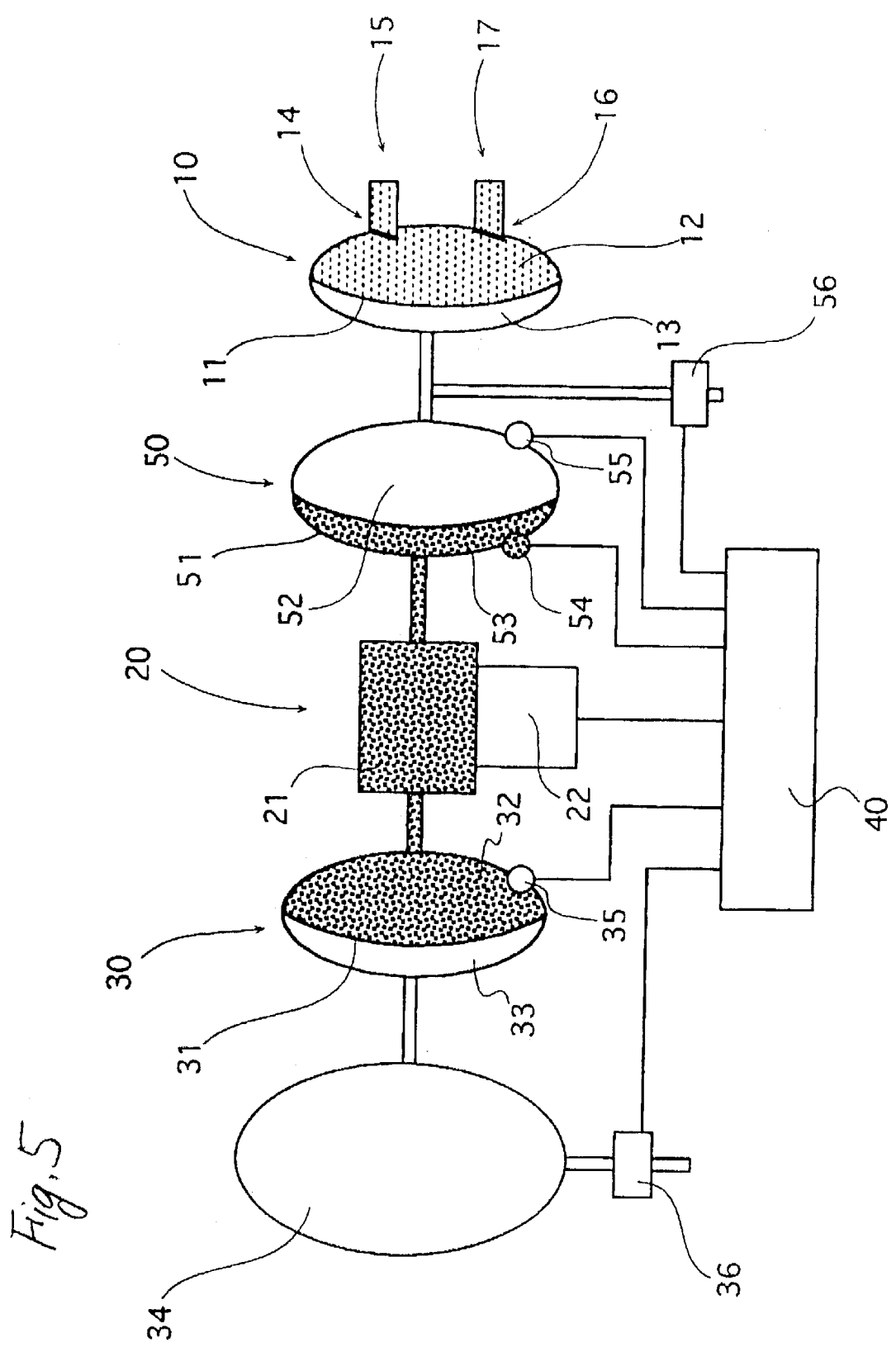
FIG. 5 illustrates a block diagram of a device for controlling a blood pump in accordance with a third embodiment of the present invention.

Referring to FIG. 5, there is illustrated a blood pump driving device in accordance with a third embodiment of the present invention which is identical with the blood pump driving device in accordance with the second embodiment, except that in the former device a pressure sensor 35 is provided in a liquid chamber 32 instead of providing the pressure sensor 35 in the pressure accumulating chamber 34 in the latter device.

So long as the diaphragm 31 in the oil reservoir 30 is not to tension, the pressure sensor 35 provided in the liquid chamber 32 can provide the same results as are provided in the pressure accumulating chamber 34 or the air chamber 33 as mentioned above. In addition to the advantages provided from each of the first and second embodiments, the third embodiment makes it possible to do a much precise control on the basis of the liquid pressure in the liquid chamber 32 and to eliminate a sensor placed close to the patient.

The invention has thus been shown and description with reference to specific embodiments, however, it should be understood that the invention is in no way limited to the details of the illustrates structures but changes and modifications may be made without departing from the scope of the appended claims.

What is claimed is:

1. A device for driving a blood pump comprising:

an oil reservoir including therein a gas chamber and a liquid chamber which are separated by a movable member;

pump means for pumping out a liquid stored in the liquid chamber of the oil reservoir to the blood pump; and a pressure accumulating chamber in fluid communication with the gas chamber of the oil reservoir for storing therein a gas pressure of the gas chamber of the oil reservoir.

2. The device as set forth in claim 1, further comprising pressure measuring means for determining the gas pressure in the gas chamber of the oil reservoir.

3. The device as set forth in claim 2, wherein the pressure measuring means is provided in the pressure accumulating chamber.

4. A device for driving a blood pump comprising:

a first port connected to the blood pump;

an oil reservoir having a gas chamber and a liquid chamber which is separated from the gas chamber by a movable member;

a second port connected to the liquid chamber; pump means for establishing positive and negative pumping actions in alternate fashion, the positive pumping action and the negative pumping action sucking and discharging a liquid from the second port and the first port to discharge the liquid to the first port and the second port, respectively;

pressure measuring means for determining a pressure in the gas chamber of the oil reservoir; and a control device controlling the positive and negative pumping actions of the pump means on the basis of a signal issued from the pressure measuring means.

5. A device as set forth in claim 4, wherein the control device calculates an amount of the liquid to be sucked from and discharged to the blood pump on the basis of a changed amount in the signal from the pressure measuring means.

6. A device as set forth in claim 4, wherein the control device switches, on the basis of the signal from the pressure measuring means, the pumping means from the positive pumping action to the negative pumping action and vice versa.

7. A device as set forth in claim 4, wherein the gas chamber is in association with the atmosphere by way of valve means so as to be brought into atmospheric pressure level when the pressure in the gas chamber becomes a negative pressure.

8. A device as set forth in claim 4, wherein one of a capacity of the gas chamber and the pressure in the gas chamber is set such that loads of the pumping means when performing the respective positive and negative pumping actions are as equal as possible.

9. A device as set forth in claim 4 further comprising a separation chamber including a second liquid chamber and a second gas chamber which are separated by a second movable member, the second liquid chamber being connected to the first port, the second liquid chamber being connected to the blood pump.

10. A device as set forth in claim 9, wherein the control device sets an amount of air in the second gas chamber on the basis of the signal from the pressure measuring means.

* * * * *